(12) United States Patent
Mirov et al.

(10) Patent No.: US 10,993,661 B1
(45) Date of Patent: *May 4, 2021

(54) WIRELESS CHARGING OF A WRIST-MOUNTED SENSOR PLATFORM

(71) Applicant: Verily Life Sciences LLC, Mountain View, CA (US)

(72) Inventors: Russell Norman Mirov, Los Altos, CA (US); John Lapetina, Los Altos Hills, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/665,931

(22) Filed: Oct. 28, 2019

Related U.S. Application Data

(63) Continuation of application No. 14/303,865, filed on Jun. 13, 2014, now Pat. No. 10,485,478.

(51) Int. Cl.
| | |
|---|---|
| *A61B 5/00* | (2006.01) |
| *A61B 5/01* | (2006.01) |
| *H02J 7/02* | (2016.01) |
| *A61B 5/1455* | (2006.01) |
| *A61B 5/0533* | (2021.01) |

(52) U.S. Cl.
CPC ............ *A61B 5/681* (2013.01); *A61B 5/01* (2013.01); *A61B 5/0533* (2013.01); *A61B 5/1455* (2013.01); *H02J 7/025* (2013.01); *Y02E 60/10* (2013.01)

(58) Field of Classification Search
CPC .......... Y02E 60/12; Y02E 60/10; H02J 7/025; H01F 38/14; Y02T 90/122; B60L 11/182; A61B 5/681; A61B 5/01; A61B 5/0533; A61B 5/1455

USPC ............................................ 320/108; 307/104
See application file for complete search history.

(56) References Cited

U.S. PATENT DOCUMENTS

| | | |
|---|---|---|
| 6,212,414 B1 | 4/2001 | Alameh et al. |
| 6,261,221 B1 | 7/2001 | Tepper et al. |
| 7,889,139 B2 | 2/2011 | Hobson et al. |
| 8,059,491 B1 | 11/2011 | Hennings-Kampa |
| 8,287,451 B2 | 10/2012 | Hu et al. |
| 8,552,684 B2 | 10/2013 | Tabata et al. |

(Continued)

FOREIGN PATENT DOCUMENTS

WO     2015079270 A1    6/2015

*Primary Examiner* — Nathaniel R Pelton
*Assistant Examiner* — Mohammed J Sharief
(74) *Attorney, Agent, or Firm* — McDonnell Boehnen Hulbert & Berghoff LLP

(57) ABSTRACT

Wearable devices are described herein including a housing and a mount configured to mount a contact surface of the housing to an external surface of a wearer. The wearable devices further include a coil disposed in the housing proximate to the contact surface and at least one sensor disposed on the contact surface and configured to detect one or more properties of the body of the wearer. The wearable devices are powered by a rechargeable battery disposed within the wearable devices. The wearable devices additionally include a recharger disposed within the wearable devices and configured to recharge the rechargeable battery using electromagnetic energy received by the coil. The sensor is disposed within a central portion of the contact surface enclosed by the coil.

18 Claims, 8 Drawing Sheets

(56) References Cited

U.S. PATENT DOCUMENTS

| | | |
|---|---|---|
| 2005/0131495 A1 | 6/2005 | Parramon et al. |
| 2005/0288743 A1* | 12/2005 | Ahn .................... A61N 1/3787 |
| | | 607/61 |
| 2008/0208009 A1 | 8/2008 | Shklarski |
| 2009/0021212 A1 | 1/2009 | Hasegawa et al. |
| 2009/0233710 A1 | 9/2009 | Roberts |
| 2012/0220835 A1 | 8/2012 | Chung |
| 2013/0043836 A1 | 2/2013 | Hui |
| 2013/0345606 A1* | 12/2013 | Ehrenreich ........ A61B 5/02208 |
| | | 601/46 |
| 2014/0065948 A1 | 3/2014 | Huang |
| 2014/0132206 A1 | 5/2014 | Zhu |
| 2014/0187157 A1 | 7/2014 | Liao |
| 2015/0173674 A1* | 6/2015 | Hayes .................. A61B 5/7278 |
| | | 600/301 |

* cited by examiner

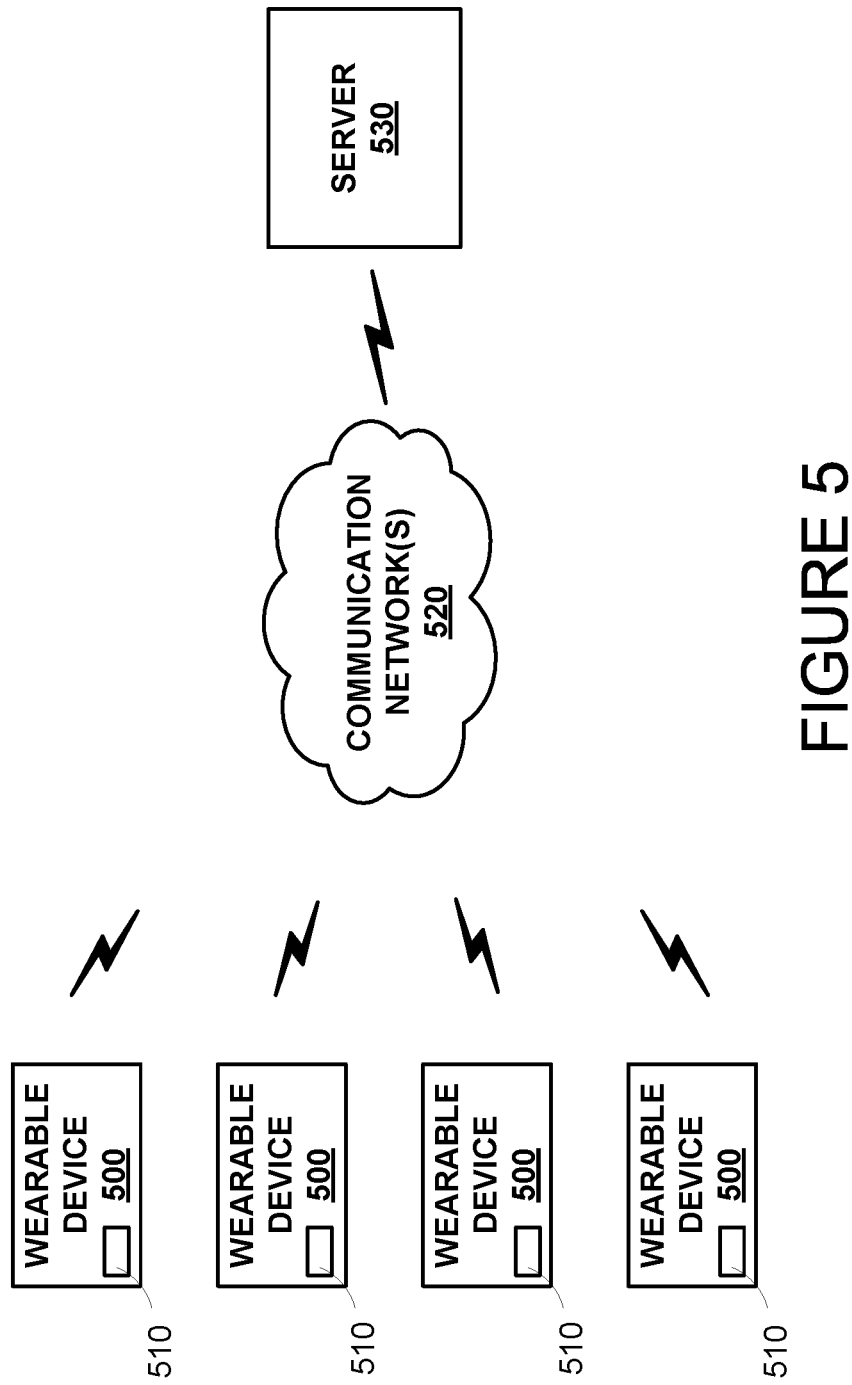

WIRELESS CHARGING OF A WRIST-MOUNTED SENSOR PLATFORM

CROSS-REFERENCE TO RELATED APPLICATIONS

This application is a continuation of U.S. patent application Ser. No. 14/303,865, filed Jun. 13, 2014, which is incorporated herein by reference.

BACKGROUND

Unless otherwise indicated herein, the materials described in this section are not prior art to the claims in this application and are not admitted to be prior art by inclusion in this section.

A number of scientific methods have been developed to detect and/or measure one or more physiological properties of a human. Some of these methods can be implemented in the form of portable, low-power sensing devices. Such sensing devices can be included in wearable devices that can be mounted to a human body to enable continuous sensing detection and/or measurement of the one or more physiological properties.

In some examples, the one or more physiological properties include properties of analytes in the human body. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout a human's body was of scientific, medical, personal, or other interest.

In some examples, the one or more physiological properties include a Galvanic skin response of skin of the human body. The Galvanic skin response is a change in the conductivity and/or electrical potential of the skin due to changes in the moisture level of the skin. This change in moisture level can be caused by activation or inactivation of sweat glands in the skin. The Galvanic skin response includes the Galvanic skin resistance (GSR), a measure of the conductivity of the skin between two or more points, and the Galvanic skin potential (GSP), a measure of the voltage difference between two or more points on the skin

SUMMARY

Some embodiments of the present disclosure provide a wearable device including: (i) a housing; (ii) a rechargeable battery disposed within the wearable device; (iii) a mount configured to mount the housing to an external body surface of a body such that a contact surface of the housing is in contact with the external body surface; (iv) a coil configured to receive electromagnetic energy, wherein the coil is disposed within the housing and proximate to the contact surface of the housing, wherein the coil comprises a plurality of windings surrounding an interior, and wherein the contact surface of the housing includes a central portion proximate to the interior of the coil and outlined by the windings of the coil; (v) a sensor disposed on the contact surface of the housing in the central portion, wherein the sensor is configured to detect one or more properties of the body via the external body surface; and (vi) electronics disposed in the wearable device, wherein the electronics comprises: (a) a recharger configured to recharge the rechargeable battery, wherein the recharger is configured to be powered by electromagnetic energy received by the coil; and (b) a controller configured to operate the sensor to detect one or more properties of the body via the external body surface.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5 is a block diagram of an example system that includes a plurality of wearable devices in communication with a server.

DETAILED DESCRIPTION

Figure 1A:
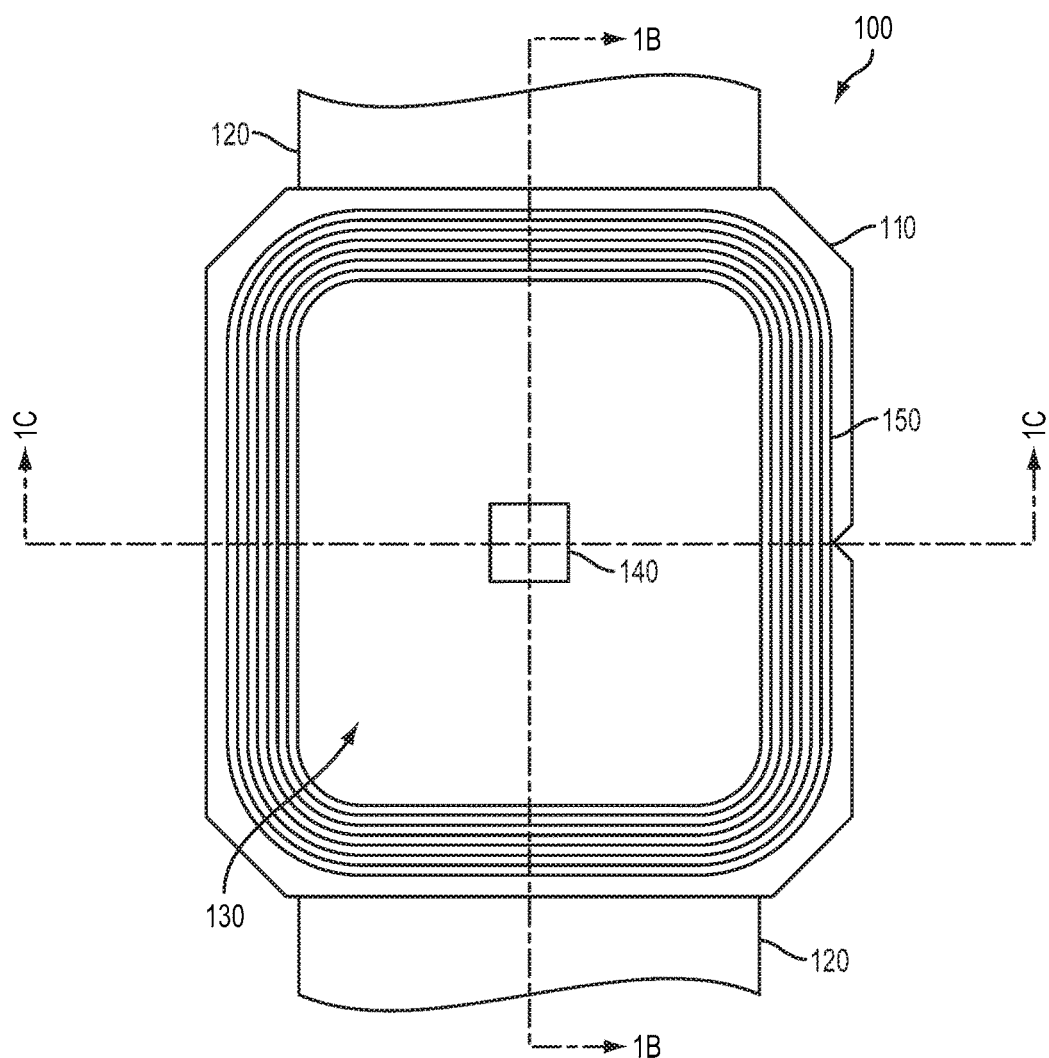
FIG. 1A is a schematic illustration of elements of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a sensor is desired, where the sensor is powered by a rechargeable battery that can be recharged using electromagnetic energy received by a coil disposed proximate to the sensor. The environment may be any living or non-living body or a portion thereof, a gel, an emulsion, a fluid conduit, a fluid reservoir, etc. For example, one of skill in the art will recognize that the embodiments disclosed herein may be used to sense analytes present in a water treatment system.

I. Overview

A wearable device may be configured to measure one or more physiological parameters of a wearer. The one or more physiological parameters can include galvanic skin response, pulse timing and/or rate, blood oxygenation, temperature, the concentration of one or more analytes in the blood, or some other parameters. To measure the one or more physiological parameters, the wearable device may include a sensor disposed in a housing of the device so as to have access to (e.g., to contact, to be able to receive light from, to be able to illuminate) the wearer's skin at a location such as the wearer's wrist, forearm, upper arm, leg, thigh, etc. With the sensor having access to the wearer's skin, electronics within the device may be used to operate the sensor to measure the one or more physiological parameters. The electronics may be powered by a rechargeable battery in the wearable device. The wearable device may further include a recharger for recharging the rechargeable battery. To recharge the rechargeable battery, the recharger may be connected to a coil configured to receive electromagnetic energy from an external source (e.g., a wireless charger).

In one example, the wearable device includes a housing (e.g., a water-proof housing) and a mount (e.g., a band) that can mount the housing on a particular body location, such as a wrist. To maximize the amount of electromagnetic energy the coil can receive, the coil can be disposed along an outer edge of the housing. The sensor can be disposed in the housing and within the extent of the coil in order to access the wearer's skin. Electronics disposed in the housing may include a reference voltage sources, current sources, amplifiers, comparators, ADCs, or other elements configured to operate the sensor to detect the one or more physiological parameters of the wearer. The electronics may also include the recharger. The recharger could be configured to operate the coil to receive electromagnetic energy of a specific frequency (e.g., to have a capacitance related to an inductance or other properties of the coil; to adjust an effective capacitance of the recharger to change the specific frequency and/or to adapt to one or more properties of the environment of the wearable device). The recharger could additionally be configured to operate the coil or other components to communicate with a wireless charger.

The wearable device could include one or more magnetic shield elements to shield components of the wearable device from electromagnetic energy (e.g., energy from a wireless charger). That is, certain components of the wearable device could experience heating or other effects when exposed to a charging electromagnetic energy (e.g., a radio-frequency EM field). Further, the one or more magnetic shield elements could be configured to increase the efficiency of energy transfer to the coil. In some examples, the one or more magnetic shield elements include a sheet composed of ferrite material or of some other material having a specified electromagnetic property (e.g., a specified low magnetic reluctance, a specified high resistivity) disposed between the coil and other elements of the wearable device (e.g., the rechargeable battery, the recharger, other electronics). In some examples, the coil and sensor are disposed on a first printed circuit (e.g., a flexible printed circuit) and connected to elements on the other side of the magnetic shield (e.g., the rechargeable battery, the recharger, other electronics) by a flexible interconnect that passes through a slot, hole, or other feature of the magnetic shield. In some examples, the sensor is disposed on a side of the magnetic shield opposite the coil and accesses (e.g., illuminates, detects light or other energy received from) the external body surface of a wearer through a hole or other feature of the magnetic shield. In some examples, the printed circuit on the coil side of the magnetic shield includes a minimal amount of metal (e.g., conductive circuit traces and/or interconnects) to reduce heating of the wearable device and/or to increase the efficiency of energy transfer to the coil. For example, the printed circuit on the coil side of the magnetic shield could lack a ground plane.

In some examples, the wearable device may include a user interface that is configured to provide user-discernible indications (e.g., visual, audible, and/or tactile indications) of one or more physiological parameters measured by the device, such as galvanic skin response, temperature, or pulse rate. In some examples, the wearable device may include a wireless communication interface that can transmit data to an external device, for example, using Bluetooth, ZigBee, WiFi, or other wireless communication protocol. The data transmitted by the wireless communication interface may include data indicative of one or more physiological parameters measured by the device.

II. Example Wearable Sensor Platforms

Wearable devices as described herein can be configured to be mounted to an external body surface of a wearer and to enable a variety of applications and functions. Such wearable devices include a housing (i.e., a rigid or semi-rigid enclosure) and a mount configured to mount a contact surface of the housing to the external body surface of the wearer. A sensor disposed on a central portion of the contact surface can detect one or more properties of the body of the wearer when the contact surface is mounted to the external body surface. A coil configured to receive electromagnetic energy is disposed within the housing, proximate to the contact surface, and windings of the coil outline the central portion of the contact surface. Such wearable devices could enable a variety of applications, including measuring physiological information about a wearer, indicating such measured physiological information or other information to the wearer (e.g., using a vibrator, a screen, a beeper), or other functions. Energy received using the coil could be used to power the wearable device and/or to recharge a rechargeable battery of the wearable device that is configured to power the wearable device.

FIG. 1A illustrates a schematic view of components of an example wearable device 100. The wearable device includes a housing 110 (e.g., a water-resistant and/or water-proof housing) configured to contain electronic components and to be mounted to an external body surface of a wearer by a mount 120 (e.g., a band). The mount 120 is a band configured to enclose a wrist of a human and to mount a contact surface 130 of the housing 110 in contact with the wrist of the wearer. A sensor 140 is disposed on a central portion of the contact surface and a coil 150 is disposed within the housing 110 proximate to the contact surface 130. The coil 150 comprises windings that outline the central portion of the contact surface 130 such that the central portion of the contact surface 130 is proximate to the interior of the coil 150. The wearable device 100 includes additional elements that are not shown, e.g., electronics configured to the operated the coil 150 and/or sensor 140 and to enable applications and/or functions of the wearable device 100, a rechargeable battery configured to power the wearable device 100, a recharger configured to recharge the rechargeable battery using electromagnetic energy received using the coil 150, or other components. Components of the wearable device 100 could be disposed on or within the housing 110, the mount 120, or some other elements of the wearable device 100 (not shown); e.g., a second housing.

The housing 110 could be configured to be water-resistant and/or water-proof. That is, the housing 110 could be configured to include sealants, adhesives, gaskets, welds, press-fitted seams, and/or other joints such that the housing 110 was resistant to water entering an internal volume or volumes of the housing 110 when the housing 110 is exposed to water. The housing 110 could further be water-proof, i.e., resistant to water entering an internal volume or volumes of the housing 110 when the housing 110 is submerged in water. For example, the housing 110 could be water-proof to a depth of 1 meter, i.e., configured to resist water entering an internal volume or volumes of the housing 110 when the housing 110 is submerged to a depth of 1 meter. Further, the interface between the housing 110 and other elements of the wearable device 100 (e.g., elements of a sensor, buttons, user interface elements, electrical contacts) protruding from, embedded in the surface of, or otherwise interrupting the material of the housing 110 could be configured such that the combination of the housing 110 and the other elements of the wearable device 100 is water-resistant and/or water-proof.

Figure 1B:
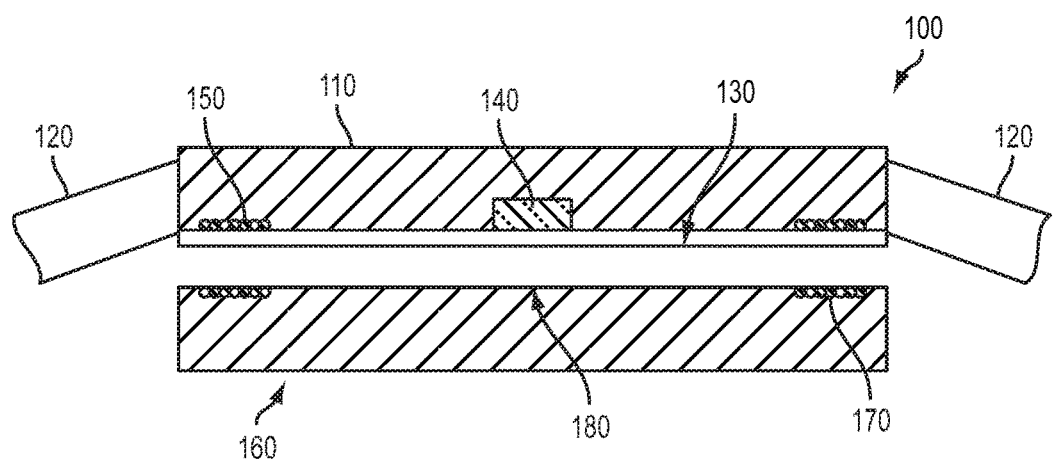
FIG. 1B is a cross-sectional schematic of the example wearable device illustrated in FIG. 1A mounted to an example wireless charger.

FIG. 1B is a cross-sectional view of the wearable device 100 mounted on a wireless charger 160. The wireless charger 160 includes a charging coil 170 configured to emit electromagnetic energy. The wearable device 100 can be mounted on (e.g., placed on, secured to, disposed in proximity to, aligned with) the wireless charger 160 such that the contact surface 130 of the wearable device 100 is in contact with a charging surface 180 of the wireless charger 160.

In some embodiments, the wearable device 100 and/or wireless charger 160 could be configured to facilitate efficient transfer of electromagnetic energy between the charging coil 170 of the wireless charger 160 and the coil 150 of the wearable device 100 by aligning, ensuring proximity of, or effecting some other specified relative arrangement between the coil 150 and the charging coil 170. For example, the wearable device 100 and/or wireless charger 160 could include elements and/or be configured to ensure alignment between the coil 150 and charging coil 170, e.g., by the contact surface 130 and the charging surface 180 having matching and/or interlocking shapes, by including one or more permanent magnets configured to exert aligning magnetic forces between the wearable device 100 and the wireless charger 160, by including alignment markings to indicate to a user a proper alignment of the wearable device 100 on the wireless charger 160, or by the addition of some other components.

Further, the wearable device 100 and/or wireless charger 160 could include one or more magnetic shims or other materials having one or more specified magnetic properties to modify the transfer of electromagnetic energy between the coil 150 and the charging coil 170. For example, the wearable device 100 could include a magnetic shield disposed proximate to the coil 150 on a side of the coil 150 opposite the contact surface 130. The magnetic shield could be configured to 'focus' electromagnetic energy directed toward the coil 150 such that the coil 150 can receive more of the electromagnetic energy. The magnetic shield could additionally or alternatively be configured to shield components of the wearable device 100 from electromagnetic energy (e.g., to prevent electromagnetic energy directed toward the wearable device 100 from heating or otherwise affecting components (e.g., electronics, rechargeable batteries) opposite the magnetic shield from the direction of the electromagnetic energy).

The coil 150 can be configured in a number of ways to enable efficient reception of electromagnetic energy using the coil 150 or to enable and/or facilitate a number of other applications. The windings of the coil 150 could be disposed proximate to a peripheral portion of the contact surface 130 of the housing 110 such that an area enclosed by the coil 150 (e.g., the central portion of the contact surface 130 of the housing 110) is maximized and/or such that a separation distance between the coil 150 and the charging coil 170 is minimized. The coil could have a rectangular shape, an elliptical shape, or some other shape according to an application; for example, the shape of the coil 150 could correspond to the shape of the contact surface 130. The coil 150, recharger (not shown), or other components could be configured to enable efficient reception of electromagnetic energy of a specific frequency (e.g., 100 kilohertz to 200 kilohertz) by the coil. For example, the coil and a capacitor of the recharger could be configured to have a resonant frequency equal to the specific frequency of the electromagnetic energy.

The wireless charger 160 could be configured in a variety of ways and include a variety of additional components to facilitate the emission of electromagnetic energy such that the coil 150 of the wearable device 100 can receive the transmitted electromagnetic energy. The wireless charger could include switches, coils, capacitors, variable frequency drives, or other electronics configured to emit electromagnetic energy that could be received by the coil 150 of the wearable device 100. In some examples, the wireless charger 160 could be configured to detect the presence, energy capacity, or other properties of the wearable device 100 and to emit electromagnetic energy having one or more properties related to the detected presence, energy capacity, or other property. In some examples, the wireless charger 160 could receive information from the wearable device 100 indicating an amount of electromagnetic energy to emit toward the coil 150 of the wearable device 100. For example, the wearable device 100 could operate the coil 150 to change the impedance or some other electromagnetically detectable property of the coil 150 in a pattern related to an amount of energy that the wireless charger 160 could emit toward the coil 150 of the wearable device 100 using the charging coil 170. In some examples, the wireless charger 160 and/or wearable device 100 could comply with one or more wireless charging standards (e.g., the Qi wireless charging standard).

Figure 1C:
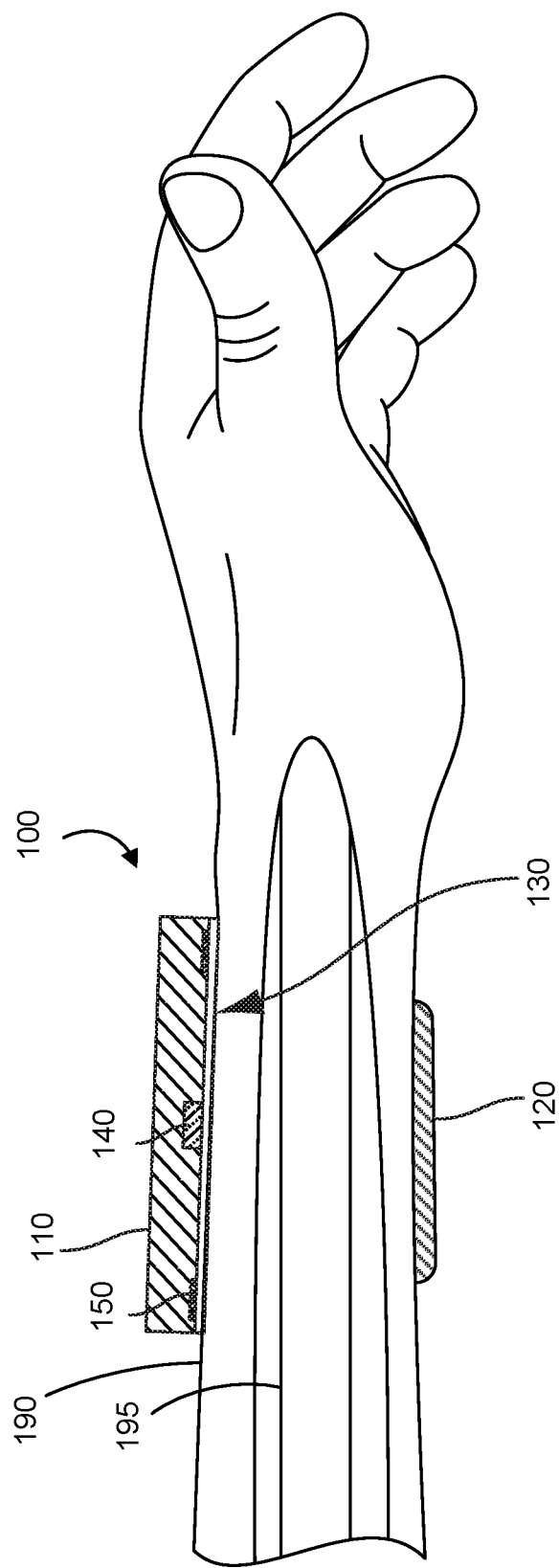
FIG. 1C is side partial cross-sectional view of the example wearable device illustrated in FIG. 1A, while on a human wrist.

FIG. 1C is a partial cross-sectional side view of a human wrist illustrating the operation of the wearable device 100 when mounted to a human wrist. In the example shown in FIG. 1C, the wearable device 100 is mounted (using the mount 120) such that the contact surface 130 is in contact with the posterior side 190 of the wearer's wrist (i.e., an external body surface of the wearer). Sensor 140 is positioned over a portion of the wrist where subsurface vasculature 195 is easily observable. The sensor 140 could be operated to detect one or more properties of the skin, subsurface vasculature 195, or other elements of the wearer's body proximate to the wearable device 100 via the posterior side 190 of the wearer's wrist, e.g., by contacting, directing energy (e.g., electrical, magnetic, illumination, acoustic waves) through/into, detecting energy (e.g., electrical, magnetic, illumination, acoustic waves) received from/through, or otherwise interacting with and/or through an external body surface of the wearer (i.e., the posterior side 190 of the wearer's wrist).

The sensor 140 is disposed on the central portion of the contact surface 130 of the housing 110 such that the sensor 140 can access the body of the wearer (i.e., make electrical, thermal or other physical contact with, receive light or other electromagnetic energy from, emit light or other electromagnetic energy toward, detect and/or emit an electric, magnetic, or other field from/to the body of the wearer) without being occluded or otherwise blocked by the coil 150. The sensor 140 accessing the body of the wearer could include the sensor being disposed outside the housing, inside the housing, proximate to a window or other hole in the housing, proximate to a filter or other element permitting partial access to the body of the wearer, or some other configuration.

The sensor 140 could include a light sensor, an IR sensor, an electric field sensor, a magnetic field sensor, an electromagnetic energy sensor, a temperature sensor, an electric current sensor, an electric potential sensor, or some other sensor or combination of sensors. The sensor 140 could include a light emitter, an IR emitter, and electromagnetic energy emitter, a heater, a vibrator, or some other energy emitter. The sensor 140 could be configured to operate in direct contact with an external body surface of the wearer (e.g., configured to include a heat- or electricity-conducting probe or other element in physical contact with the skin of the wearer to facilitate detection of one or more properties of the body of the wearer). The sensor 140 could be configured to detect a Galvanic skin resistance of skin at the external body surface of the wearer by applying an electric potential between two probes in electrical contact with skin at the external body surface of the wearer.

The sensor 140 could interact with and/or detect one or more properties of specific elements or components of the body of the wearer. In some examples, the sensor 140 could act to illuminate or otherwise direct energy toward elements in the body of the wearer and could detect a light or other energy emitted by, reflected by, scattered by, or otherwise received from the elements in response to the illumination and/or direction of energy toward the elements. For example, the sensor 140 could be configured to illuminate a fluorophore, chromophore, or other optic chemical, moiety, analyte, or other element of the body of the wearer and to detect light emitted, scattered, reflected, or otherwise received from the element of the body of the wearer in response to the illumination. One or more properties of the illumination and/or of the detected light could be used to determine one or more properties of the body of the wearer. For example, a degree of scattering of light having a specified wavelength could be used to determine a pulse rate of the wearer, a blood oxygenation of blood in the skin and/or subsurface vasculature 195 of the wearer, or some other property of the body of the wearer.

In some examples, the coil 150 could be operated to facilitate some application of the sensor 140. For example, the coil 150 could be operated to emit an electromagnetic energy having a specified frequency when the wearable device 100 is mounted to the external body surface of the wearer. The electromagnetic energy could excite, apply a force to, or otherwise interact with some element of the body of the wearer such that the sensor 140 could detect one or more properties of the body of the wearer. Other methods of operation of the coil 150 to enable detection of one or more properties of the body of the wearer are anticipated.

In some examples, the body of the wearer (e.g., the subsurface vasculature 195) could include artificial or other contrast agents (e.g., fluorophores, fluorescent nanodiamonds, chromophores, acoustic particles, magnetic particles) functionalized or otherwise configured to enable the detection of one or more properties of the body of the wearer using the sensor 140. For example, a contrast agent including a fluorophore could be configured to selectively bind to an analyte of interest in the blood of the wearer, and sensor 140 could be operated to determine to presence, location, binding state, or other properties of the contrast agent in the blood. The determined one or more properties of the contrast agent could be used to determine the presence or concentration of the analyte in the blood of the wearer. Other contrast agents, properties of the body of the wearer, and configurations and method of operation of the sensor 140 are anticipated.

Figure 2A:
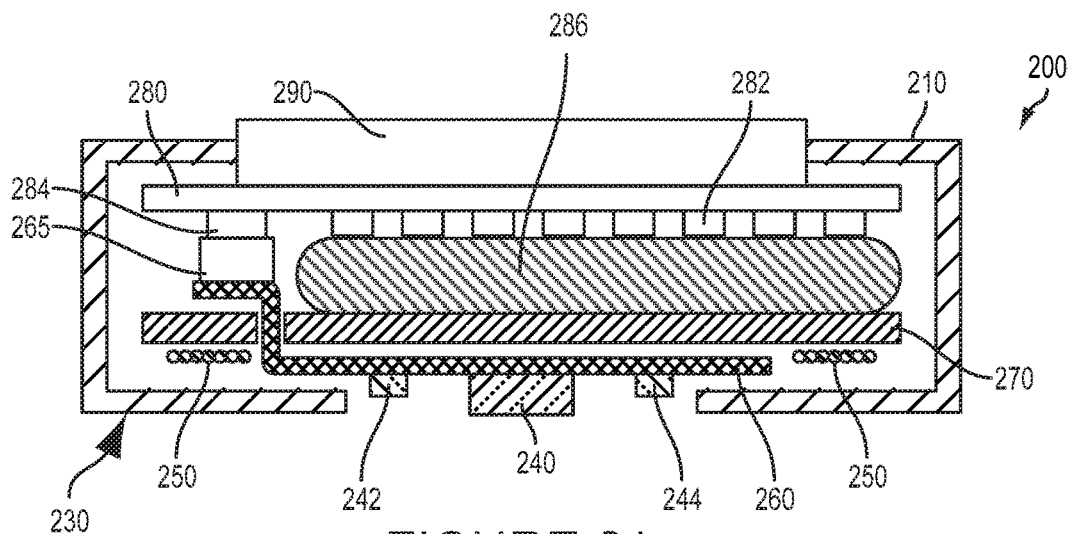
FIG. 2A is a cross-sectional schematic of an example wearable device.
Figure 2B:
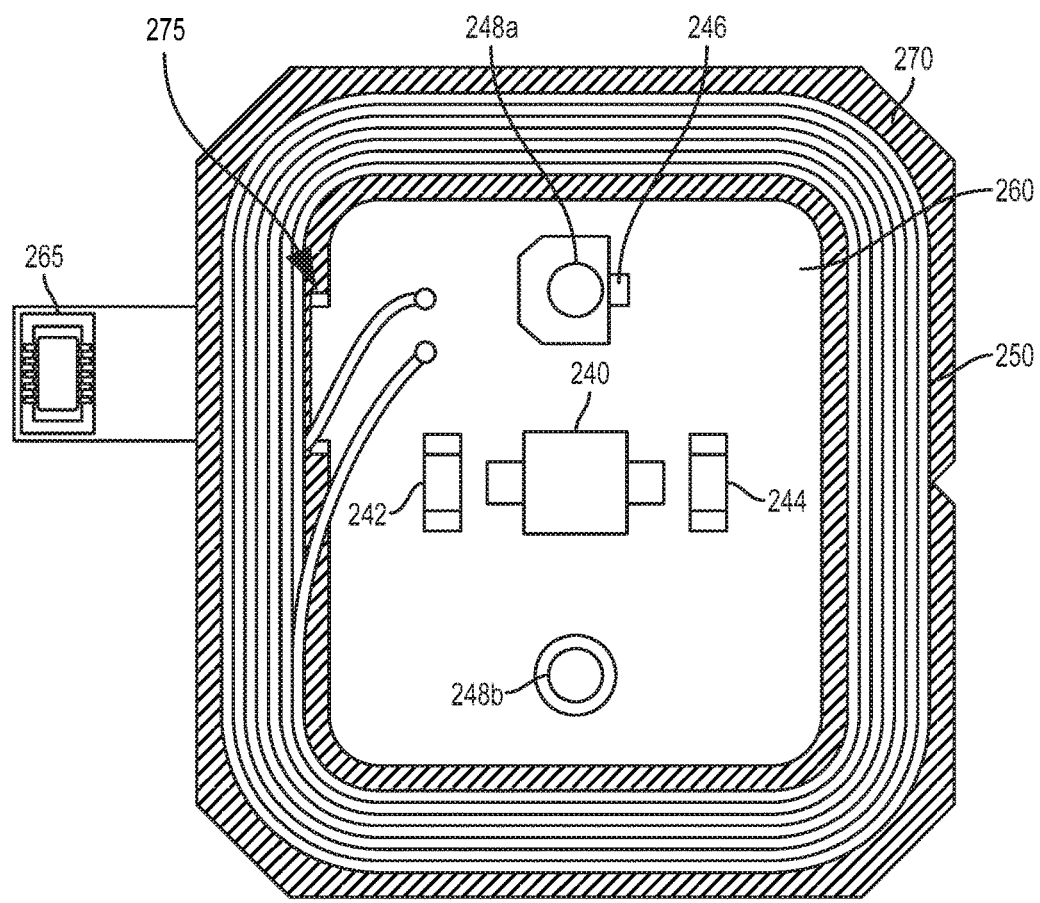
FIG. 2B is an illustration of elements of the example wearable device illustrated in FIG. 2A.

Wearable devices and other embodiments as described herein can include a variety of components configured in a variety of ways. FIG. 2A illustrates a cross-sectional schematic view of a wearable device 200 that includes a housing 210 (e.g., a water-resistant and/or water-proof housing) and mount (e.g., a band 220, as shown in FIG. 2D) configured to mount a contact surface 230 of the housing to an external body surface (e.g., a wrist) of a wearer. The housing 210 contains a coil 250 disposed within the housing 210 proximate to the contact surface 230 that is configured to receive electromagnetic energy. The wearable device 200 additionally includes a variety of sensors and components of sensors (e.g., 240, 242, 244) disposed on the contact surface 230 and configured to detect one or more properties of the body of the wearer. FIGS. 2B and 2D illustrate other sensors and components of sensors (246, 248a, 248b, 249a, 249b) included in the wearable device 200.

The sensors and components of sensors are mounted on a flexible printed circuit board (PCB) 260 that is mounted onto a magnetic shield 270. The coil 250 is also disposed on the magnetic shield 270 and is electronically coupled to the flexible PCB 260. A flexible interconnect of the flexible PCB 260 passes through a slot 275 in the magnetic shield 270 and includes a first connector 265 that is connected to a second connector 284 that is disposed on a circuit board 280 on the opposite side of the magnetic shield 270 from the coil 250 and the sensors and components of sensors (240, 242, 244, 246, 248a, 248b, 249a, 249b). Electronics 282 are also disposed on the circuit board 280. An interface 290 and a rechargeable battery 286 are operatively coupled to the circuit board 280 and disposed within the housing 210 on the same side of the magnetic shield 270 as the circuit board 280 and electronics 282 disposed thereupon.

The electronics 282 could include a variety of different components configured in a variety of ways to enable applications of the wearable device. The electronics 282 could include controllers, amplifiers, switches, display drivers, touch sensors, wireless communications chipsets (e.g., Bluetooth radios or other radio transceivers and associated baseband circuitry to enable wireless communications between the wearable device 200 and some other system(s)), or other components. The electronics 282 include a controller configured to operate one or more sensors and/or components of sensors (e.g., 240, 242, 244, 246, 248a, 248b, 249a, 249b) to detect one or more properties of the body of the wearer. The controller could include a processor configured to execute computer-readable instructions (e.g., program instructions stored in data storage of the wearable device 200) to enable applications of the wearable device 200. The electronics 282 additionally includes a recharger that is configured to recharge the rechargeable battery 286 and that is configured to be powered by electromagnetic energy received by the coil 250 (i.e., the recharger is configured to recharge the rechargeable battery 286 using energy received by the coil 250). The electronics 282 can include additional or alternative components according to an application of the wearable device 200.

The rechargeable battery 286 is configured to power the wearable device 200 using stored electrochemical energy and to be recharged a plurality of times. The rechargeable battery 286 could include one or more of a variety of rechargeable battery chemistries, including lead-acid, nickel-metal-hydride, nickel-cadmium, lithium-ion, lithium-polymer, or some other rechargeable battery chemistry. The recharger of the electronics 282 could be configured to recharge the rechargeable battery 286 by applying a constant current, a constant voltage, a trickle current, or some other electrical energy having one or more specified properties to two or more electrodes of the rechargeable battery 286. The rechargeable battery 286 could include one or more thermistors that the controller, the recharger, or some other component of the wearable device 200 could operate to determine a temperature of the rechargeable battery 286 and to prevent damage of the rechargeable battery 286 by reducing a charging rate, a discharging rate, or some other property of use of the rechargeable battery 286 to prevent damage of the rechargeable battery 286.

The interface 290 includes a display configured to present an image to a wearer and to detect one or more finger presses of a wearer on the interface 290. The controller or some other component(s) of the electronics 282 could operate the interface 290 to provide a user interface to a wearer or other user of the device and to enable the wearer or other user to affect the operation of the wearable device 200, to determine some property of the wearable device 200 and/or of the wearer of the wearable device 200, or to provide some other functionality or application to the wearer and/or user. For example, the interface 290 could be operated to indicate to the wearer one or more properties of the body of the wearer (e.g., a GSR of the skin of the wearer proximate to the wearable device 200, a pulse rate of the wearer, some other medical condition or state of the wearer). For example, the wearer could press an indicated region of the interface 290 to indicate that the wearable device 200 should begin logging detected medical information about the wearer. Other indicated information, changes in operation of the wearable device 200, or other functions and applications of the interface 290 are anticipated.

Figure 2C:
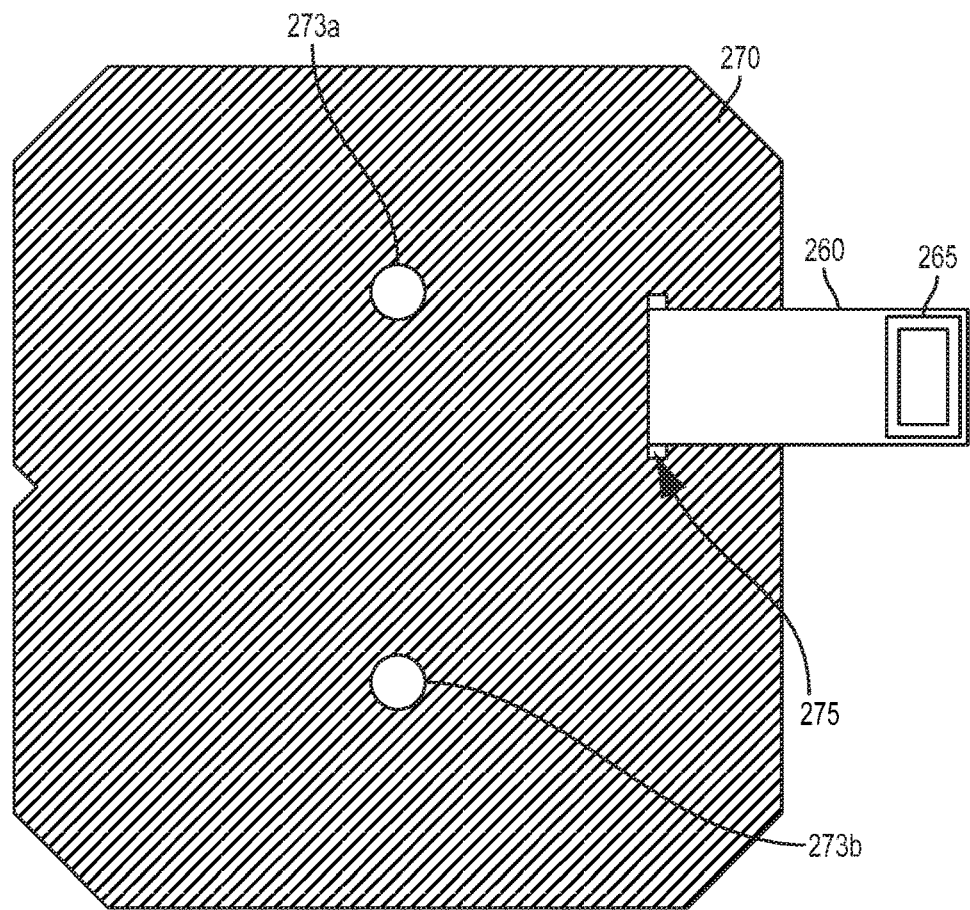
FIG. 2C is an illustration of a reverse view of the elements illustrated in FIG. 2B.
Figure 2D:
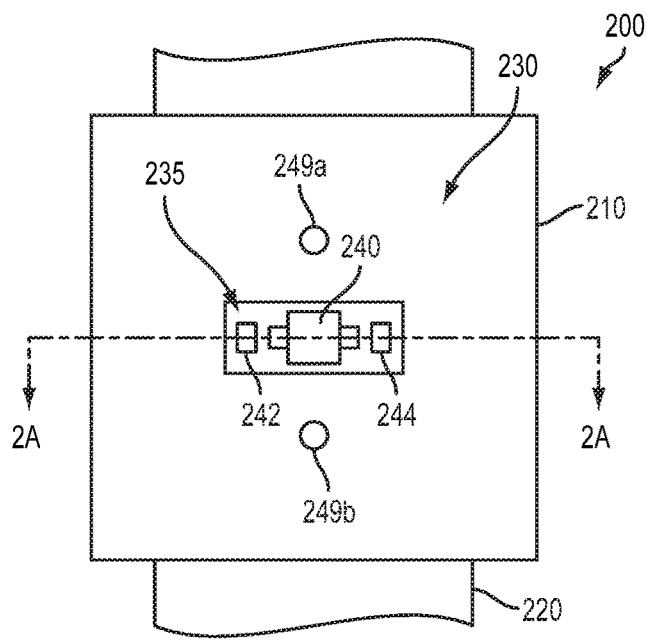
FIG. 2D is an illustration of a surface of the example wearable device illustrated in FIG. 2A.

FIGS. 2B and 2C show front and back views, respectively (i.e., a views from the direction of the contact surface 230 and opposite the contact surface 230, respectively) of elements of the wearable device 200. Specifically, FIGS. 2B and 2C illustrate the magnetic shield 270, flexible PCB 260, and some of the components disposed on the magnetic shield 270 and/or flexible PCB 260 (e.g., 265, 250, 240, 242, 244, 246, 248a, 248b). The coil 250 is disposed on the magnetic shield 270 such that when the coil 250, magnetic shield 270, and other components are assembled into the housing 210 of the wearable device as shown in FIG. 2A, the coil 250 is proximate to the contact surface 230 of the housing 210 such that windings of the coil 250 outline a central portion of the contact surface 230 proximate to the interior of the coil 250.

Further, the sensors and/or components of sensors (e.g., 240, 242, 244, 246, 248a, 248b, 249a, 249b) are disposed on the flexible PCB 260 such that, when assembled into the housing 210 of the wearable device as shown in FIG. 2A, the sensors and/or components of sensors are disposed on the contact surface 130 in the central portion of the contact surface 130. The flexible PCB 270 includes a flexible interconnect that passes through the slot 275 in the magnetic shield 270. The flexible interconnect is configured to electrically couple the electronics 282 to the coil 250 and the one or more sensors and/or components of sensors (e.g., through the connectors 265, 284, the circuit board 280, and through traces patterned on the flexible interconnect). Note that, in come embodiments, the flexible interconnect could include a cable, discrete wires, a second flexible PCB electrically connected to the flexible PCB 270, or some other element(s) configured to pass through a hole, slot, or other feature of the magnetic shield 280 and to electrically couple the coil 250 and sensors and/or components of sensors on a first side of the magnetic shield 270 to one or more electronic components on a second side of the magnetic shield 270 opposite the first side.

In some embodiments, one or more sensors could be disposed on the circuit board 280 or some other location on a side of the magnetic shield 270 opposite the coil 250 and could access (e.g., illuminate, detect light or other energy received from) the external body surface of a wearer through a hole or other feature of the magnetic shield 270.

The magnetic shield 270 is composed of one or more materials having specified magnetic properties such that, when electromagnetic energy is directed toward the wearable device 200 from the direction of the contact surface 230 such that the coil 250 can receive a portion of the directed electromagnetic energy, the electronics 282, rechargeable battery 286, and/or other components on a side of the magnetic shield 270 opposite the coil 250 are heated less by that directed electromagnetic energy than if the magnetic shield 270 was not present. That is, the magnetic shield 270 is configured to act as a shield to protect the electronics 282, rechargeable battery 286, and/or other components on a side of the magnetic shield 270 opposite the coil 250 from heating, radio-frequency noise, and/or other effects of electromagnetic energy directed at the coil 250 to provide the wearable device 200 with energy (e.g., energy that can be used to recharge the rechargeable battery 286). The magnetic shield 270 could also be configured to increase an efficiency of energy transfer between an emitter of electromagnetic energy and the coil 250. For example, the magnetic shield 270 could be configured to increase a coupling between the coil 250 and a charging coil that is directing electromagnetic energy toward the coil 250 (e.g., by concentrating within the magnetic shield 250 magnetic flux that passes through the windings of the coil 250 such that the more of the magnetic flux acts to transfer energy to the coil 250). For example, the magnetic shield 270 could be wider than the coil 250 by at least 0.5 millimeters.

The magnetic shield 270 could include materials having a specified high permeability such that the magnetic shield 270 could redirect magnetic flux to reduce heating of the electronics 282 and/or rechargeable battery 286 due to electromagnetic energy directed toward the coil 250 and/or to increase the efficiency of energy transfer to the coil 250 from electromagnetic energy directed toward the coil 250 (e.g., by a charging coil of a wireless charger). The magnetic shield 270 could include materials having a specified low electrical conductivity such that the magnetic shield 270 is minimally heated by exposure to time-varying electromagnetic fields (i.e., the magnetic shield 270 could experience minimal eddy currents when exposed to time-varying magnetic fields). The magnetic shield 270 could include soft magnetic materials, zinc ferrite, alpha iron, iron oxides, nickel, zinc, manganese, or oxides, alloys, or other combinations of these or other materials having specified magnetic properties.

The magnetic shield 270 additionally includes two mounting holes 273a, 273b configured to facilitate the assembly of the magnetic shield 270 and other elements of the wearable device 200. For example, screws, bolts, or other fasteners could pass through the mounting holes 273a, 273b to attach elements of the wearable device 200 (e.g., the housing 210, the circuit board 280, the interface 290) to other elements of the wearable device 200 (e.g., electrical contacts 229a, 249b used to detect a GSR of skin of a wearer and/or to enable other applications of the wearable device 200). Other configurations of the magnetic shield 270 and/or additional or alternative magnetic elements (e.g., magnetic cores configured to focus flux through the windings of the coil 250, ferrite cans, laminated sheets of magnetic material configured to minimize eddy current losses) are anticipated. For example, the magnetic shield 270 and/or other magnetic materials of the wearable device 200 could be magnetized or have some other magnetic property such that the wearable device 200 experiences an aligning magnetic force when mounted on a wireless charging device.

The flexible PCB 260 and components disposed thereupon could be configured to increase the efficiency of electromagnetic energy reception by the coil 250. For example, very few components could be disposed on the flexible PCB 260. For example, the wearable device may include a blood oxygenation and pulse oximetry sensor that includes a photodiode 240 and two light-emitting diodes (LEDs) 242, 244. Amplifiers, current sources, controllers, ADCs, and other components of the blood oxygenation and pulse oximetry sensor could be disposed on the circuit board 280 on the opposite side of the magnetic shield 270 from the coil 250 while only elements of the sensor requiring direct access to the body of a wearer (e.g., the photodiode 240 and LEDS 242, 244 and a minimum of metallic tracing patterned on the flexible PCB 260 to electrically couple the photodiode 240 and LEDS 242, 244 to the other components of the sensor) are disposed on the flexible PCB 260. In general, a minimum of conductive material could be disposed on the flexible PCB 260 (e.g., printed circuit traces, electronic components). In some examples, regions of the flexible PCB 270 that do not feature traces could not include conductive material. For example, the flexible PCB 270 could lack ground planes, shield planes, signal or other large 'pours' or other large contiguous regions wholly or partially covered with conductive material.

The windings of the coil 250, when assembled into the wearable device 200, are disposed proximate to a peripheral portion of the contact surface 230 of the housing 210. The coil 250 could be configured in this way to maximize the area enclosed by the coil 250 while remaining disposed within the housing 210. The windings of the coil 250 could be configured differently according to an application. For example, the coil 250 could include figure-eight windings, multiple discrete sets of windings, windings having a rectangular shape, windings having an elliptical shape, or other patterns, shapes, or configurations according to an application. In some examples the coil 250 could be disposed on the flexible PCB 260. For example, one or more windings of the coil 250 could be a trace on the flexible PCB 260. One or more properties of the coil 250 could be specified according to an application. In some examples, the coil 250 could have a substantially rectangular shape and a size of approximately 30 millimeters by 22 millimeters, corresponding to an internal shape and size of the periphery of the housing 210 of the wearable device 200. The shape, size, number of windings, and other properties of the coil, 250 (as well as properties of components of a recharger powered by electromagnetic energy received by the coil 250) could be specified such that the coil is able to receive electromagnetic energy having a specified frequency. The specified frequency could be in the range of 100 kilohertz to 200 kilohertz. The specified frequency could be specified by a wireless charging standard or standards (e.g., the Qi wireless charging standard).

Sensors of the wearable device configured to detect one or more properties the body of a wearer of the wearable device 200 could include a variety of components and could function using a variety of different mechanisms. The sensors could include light sensors, sound sensors, vibration sensors, electrical sensors (e.g., current sensors, electric field sensors, voltage sensors), electrical contacts or probes, magnetic sensors, electromagnetic energy sensors, acoustic sensors, accelerometers, pressure sensors, IR sensors, cameras, temperature sensors, or other sensors or combinations of sensors. Further, the sensors could be active sensors or could otherwise include energy emitters, including but not limited to light emitters, LEDs, lasers, electromagnetic energy emitters, emitter antennas, emitter coils, microwave emitters, magnetic field emitters, magnets, IR emitters, UV emitters, vibrators, or other energy emitting elements or combinations of energy emitting elements.

The sensors could be operated to detect one or more of a variety of properties of a wearer of the wearable device 200 via an external body surface of the wearer e.g., by contacting, directing energy (e.g., electrical, magnetic, illumination, acoustic waves) through/into, detecting energy (e.g., electrical, magnetic, illumination, acoustic waves) received from/through, or otherwise interacting with and/or through an external body surface of the wearer (i.e., skin of the wearer's wrist). For example, light could be emitted (e.g., using the LEDs 242, 244) toward an external body surface of a wearer to illuminate the external body surface, and one or more properties of light received from the external body surface could be detected (e.g., using the photodiode). This illumination and detection could be used to detect an oxygenation state of blood proximate to the wearable device (e.g., in the skin of the external body surface), a heart rate of the wearer, a flow profile of the blood in vasculature of the wearer, or some other information. The sensors could be configured to detect one or more properties of a contrast agent (e.g., a functionalized fluorophore, chromophore, magnetic particle, or some other natural or artificial contrast agent) in the body of the wearer proximate to the wearable device 200 according to an application.

In some examples, contacts could protrude from the wearable device 200 and could facilitate physical measurement of properties of the body of the wearer (e.g., of the skin at the external body surface). FIG. 2D illustrates a view of the contact surface 230 of the wearable device 200, including two circular, rounded contacts 249a, 249b configured to protrude from the contact surface 230 and to make electrical and/or thermal contact with skin of the external body surface of the wearer. The contacts 249a, 249b are in electrical contact with electrical pads 248a, 248b, respectively, on the flexible PCB 260 such that a GSR of the skin at the external body surface can be detected by the wearable device 200 (e.g., by using components of the electronics 282 to apply a specified voltage between the contacts 249a, 249b and detecting a current through the contacts 249a, 249b related to the GSR of the skin proximate to the contacts 249a, 249b). One of the contacts 249a is additionally in thermal contact with a thermometer 246 disposed on the flexible PCB 260 such that the temperature at the external body surface of a wearer could be detected by the thermometer 246 using the first contact 249a. Other uses and configurations of electrical, thermal, or other physical contacts (e.g., 249a, 249b) are anticipated.

One or more components of the sensors could be disposed on the contact surface 230 of the housing 210 such that the one or more components could access (e.g., detect a property of, emit energy toward, illuminate, physically contact) an external body surface of a wearer. The one or more components could be disposed proximate to a window, filter, grate, hole, or other feature of the housing 210 to facilitate operate of the sensor. The housing 210 includes a window 235 through which the LEDs 242, 244 can illuminate skin of the external body surface of the wearer. The photodiode 240 is also positioned proximate to the window 235 to enable the photodiode 240 to receive light from the external body surface. The window 235 could be fitted with a wholly or partially transparent window or other filter to enable the housing 210 to be water-resistant and/or water-proof. Additionally or alternatively, the housing 210 could be configured to include sealants, adhesives, gaskets, welds, press-fitted seams, and/or other joints such that the housing 210 was resistant to water entering an internal volume or volumes of the housing 210 when the housing 210 is exposed to water. The housing 210 could further be water-proof, i.e., resistant to water entering an internal volume or volumes of the housing 210 when the housing 210 is submerged in water. For example, the housing 210 could be water-proof to a depth of 1 meter, i.e., configured to resist water entering an internal volume or volumes of the housing 210 when the housing 210 is submerged to a depth of 1 meter. Further, the interface between the housing 210 and other elements of the wearable device 200 (e.g., elements of a sensor, buttons, user interface elements, electrical contacts) protruding from, embedded in the surface of, or otherwise interrupting the material of the housing 210 could be configured such that the combination of the housing 210 and the other elements of the wearable device 200 is water-resistant and/or water-proof.

Note that the embodiments illustrated in FIGS. 2A-D are illustrative examples and not meant to be limiting. Alternative embodiments, including more or fewer components in alternative configurations are anticipated. A wearable device could include multiple housings or other such assemblies each containing some set of components to enable applications of such a wearable device. For example, a wearable device could include a first housing within which are disposed a coil configured to received electromagnetic energy and a sensor configured to detect one or more properties of a wearer and a second housing containing a rechargeable battery and electronics configured to recharge the rechargeable battery using energy received using the coil. Wearable device could be configured to perform a variety of functions and to enable a variety of applications. Wearable devices could be configured to operate in concert with other devices or systems; for example, wearable devices could include a wireless communication interface configured to transmit data indicative of one or more properties of the body of a wearer of the wearable device. Other embodiments, operations, configurations, and applications of a wearable device as described herein are anticipated.

III. Example Devices

Figure 3:
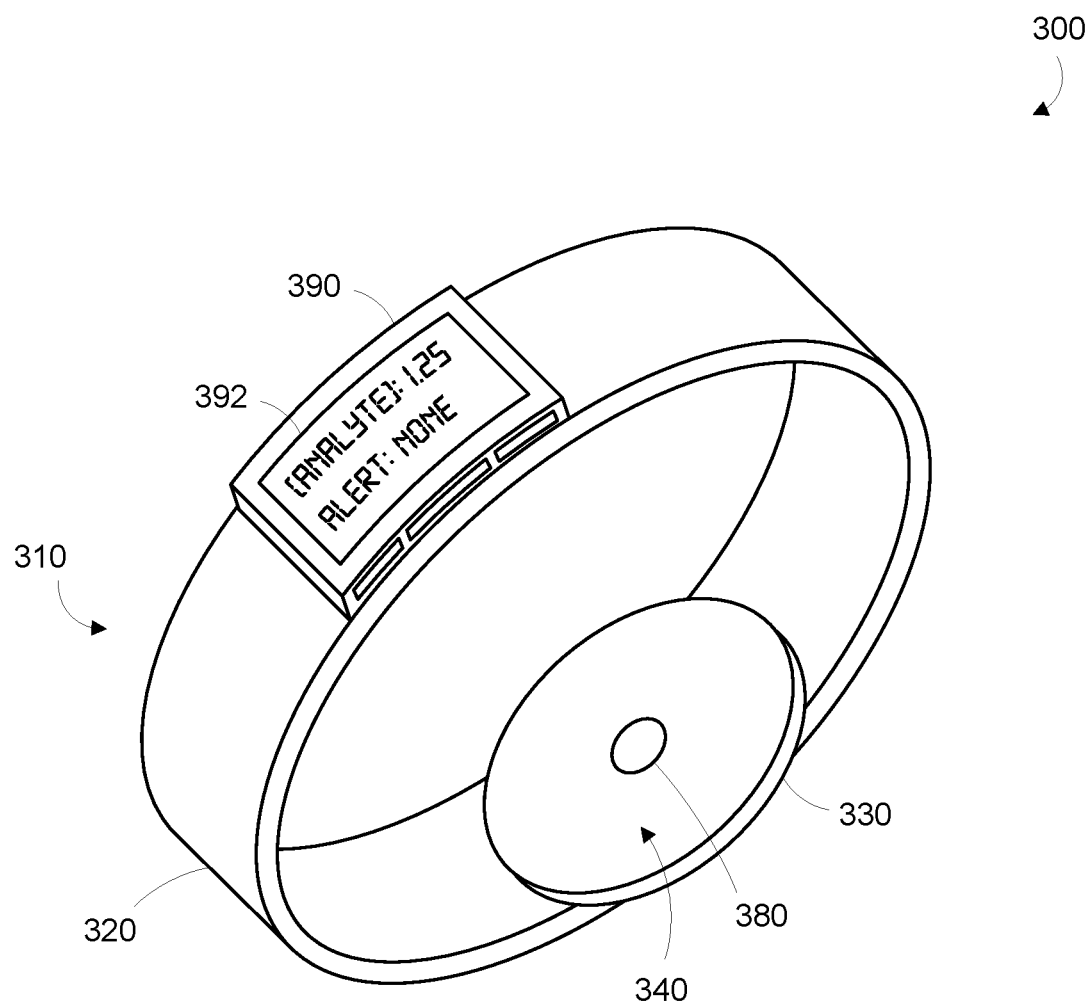
FIG. 3 is a perspective view of an example wearable device.

A wearable device 300 (illustrated in FIG. 3) can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other elements of the body of the wearer are easily observable, the qualification of which will depend on the type of detection system used. The device may be placed in close proximity to the skin or tissue. A mount 310, such as a belt, wristband, ankle band, etc. can be provided to mount the device at, on or in proximity to the body surface. The mount 310 may prevent the wearable device from moving relative to the body to reduce measurement error and noise. In one example, shown in FIG. 3, the mount 310, may take the form of a strap or band 320 that can be worn around a part of the body. Further, the mount 310 may be an adhesive substrate for adhering the wearable device 300 to the body of a wearer.

A housing 330 is disposed on the mount 310 such that it can be positioned on the body. A contact surface 340 of the housing 330 is intended to be mounted facing to the external body surface. The housing 330 may include at least one sensor 380 for detecting at least one property of the body of the wearer, which could include any parameters that may relate to the health of the person wearing the wearable device. For example, the sensor 380 could be configured to measure blood pressure, pulse rate, respiration rate, skin temperature, etc. In a non-exhaustive list, sensor 380 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. Components disposed in the housing 330 may be miniaturized so that the wearable device may be worn on the body without significantly interfering with the wearer's usual activities.

The housing 330 additionally encloses a coil (not shown) configured to received electromagnetic energy. The coil could be disposed proximate to the contact surface 340 of the housing 330 such that the coil could efficiently receive electromagnetic energy emitted by a wireless charger (not shown) when the wearable device 300 is mounted on such a wireless charger. The wearable device additionally includes a rechargeable battery (not shown) configured to power the wearable device 300. A recharger (not shown) of the wearable device 300 is configured to recharge the rechargeable battery using electromagnetic energy received using the coil. The wearable device additionally includes electronics configured to enable functions of the wearable device 300 including operating the sensor 380 to detect one or more properties of the body of a wearer.

The wearable device 300 may also include a user interface 390 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 390 may include a display 392 where a visual indication of the alert or recommendation may be displayed. The display 392 may further be configured to provide an indication of the measured physiological parameters, for instance, the concentrations of certain blood analytes being measured.

Figure 4A:
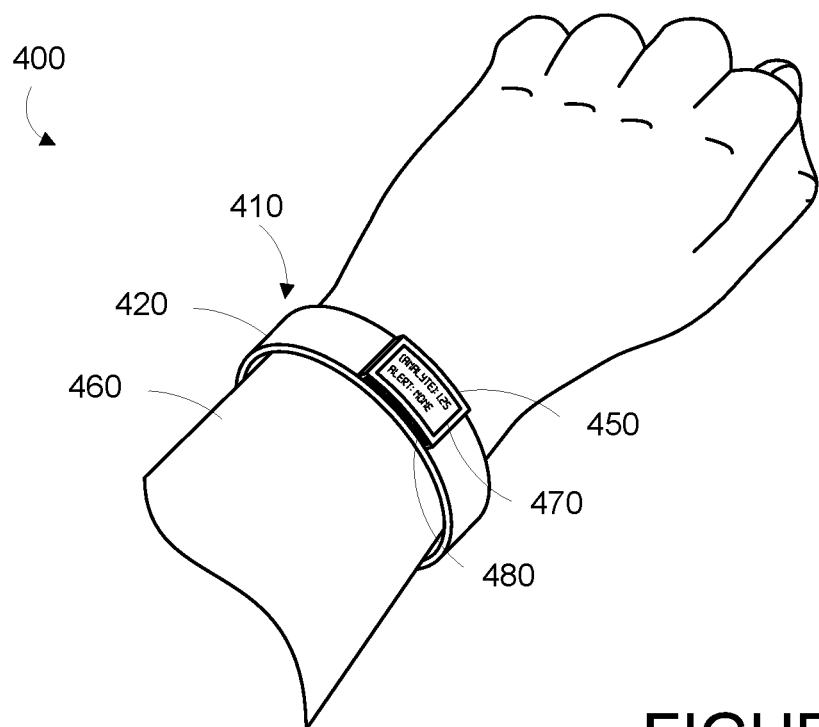
FIG. 4A is a perspective top view of an example wrist-mounted device, when mounted on a wearer's wrist.
Figure 4B:
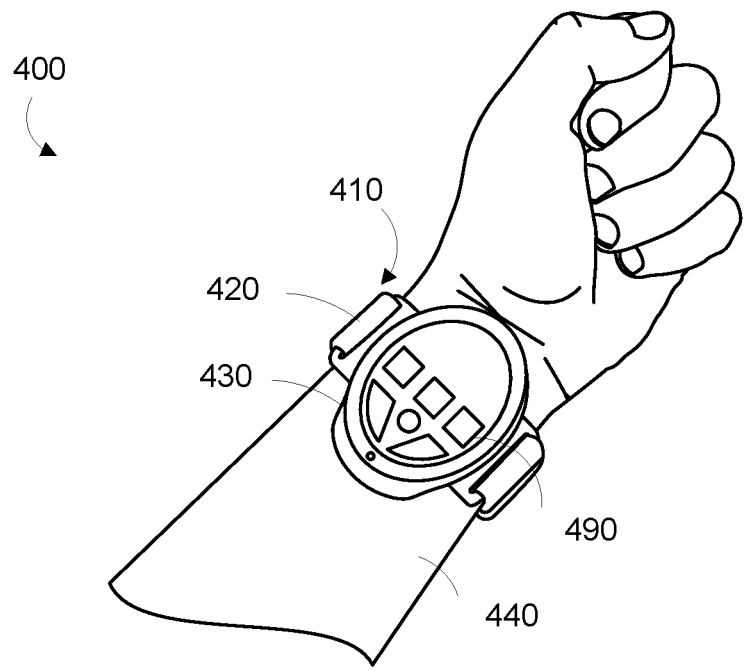
FIG. 4B is a perspective bottom view of an example wrist-mounted device shown in FIG. 4A, when mounted on a wearer's wrist.

In some examples, the wearable device is provided as a wrist-mounted device, as shown in FIGS. 4A and 4B. The wrist-mounted device may be mounted to the wrist of a living subject with a wristband or cuff, similar to a watch or bracelet. As shown in FIGS. 4A and 4B, the wrist mounted device 400 may include a mount 410 in the form of a wristband 420, a housing 430 positioned on the anterior side 440 of the wearer's wrist, and a user interface 450 positioned on the posterior side 460 of the wearer's wrist. The wearer of the device may receive, via the user interface 450, one or more recommendations or alerts generated either from a remote server or other remote computing device, or alerts from the measurement platform. Such a configuration may be perceived as natural for the wearer of the device in that it is common for the posterior side 460 of the wrist to be observed, such as the act of checking a wrist-watch. Accordingly, the wearer may easily view a display 470 on the user interface. Further, the housing 430 may be located on the anterior side 440 of the wearer's wrist where the subsurface vasculature or other elements of the body of the wearer may be readily observable. However, other configurations are contemplated.

The display 470 may be configured to display a visual indication of the alert or recommendation and/or an indication of the measured physiological parameters, for instance, the presence or concentrations of certain blood analytes being measured. Further, the user interface 450 may include one or more buttons 480 for accepting inputs from the wearer. For example, the buttons 480 may be configured to change the text or other information visible on the display 470. As shown in FIG. 4B, housing 430 may also include one or more buttons 490 for accepting inputs from the wearer. The buttons 490 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

FIG. 5 is a simplified schematic of a system including one or more wearable devices 500. The one or more wearable devices 500 may be configured to transmit data via a communication interface 510 over one or more communication networks 520 to a remote server 530. In one embodiment, the communication interface 510 includes a wireless transceiver for sending and receiving communications to and from the server 530. In further embodiments, the communication interface 510 may include any means for the transfer of data, including both wired and wireless communications. For example, the communication interface may include a universal serial bus (USB) interface or a secure digital (SD) card interface. Communication networks 520 may be any one of may be one of: a plain old telephone service (POTS) network, a cellular network, a fiber network and a data network. The server 530 may include any type of remote computing device or remote cloud computing network. Further, communication network 520 may include one or more intermediaries, including, for example wherein the wearable device 500 transmits data to a mobile phone or other personal computing device, which in turn transmits the data to the server 530.

In addition to receiving communications from the wearable device 500, such as collected physiological parameter data and data regarding health state as input by the user and/or one or more properties of a wearer detected using a sensor disposed in the wearable device 500, the server may also be configured to gather and/or receive either from the wearable device 500 or from some other source, information regarding a wearer's overall medical history, environmental factors and geographical data. For example, a user account may be established on the server for every wearer that contains the wearer's medical history. Moreover, in some examples, the server 530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Example Electronics Platform for a Device

Figure 6:
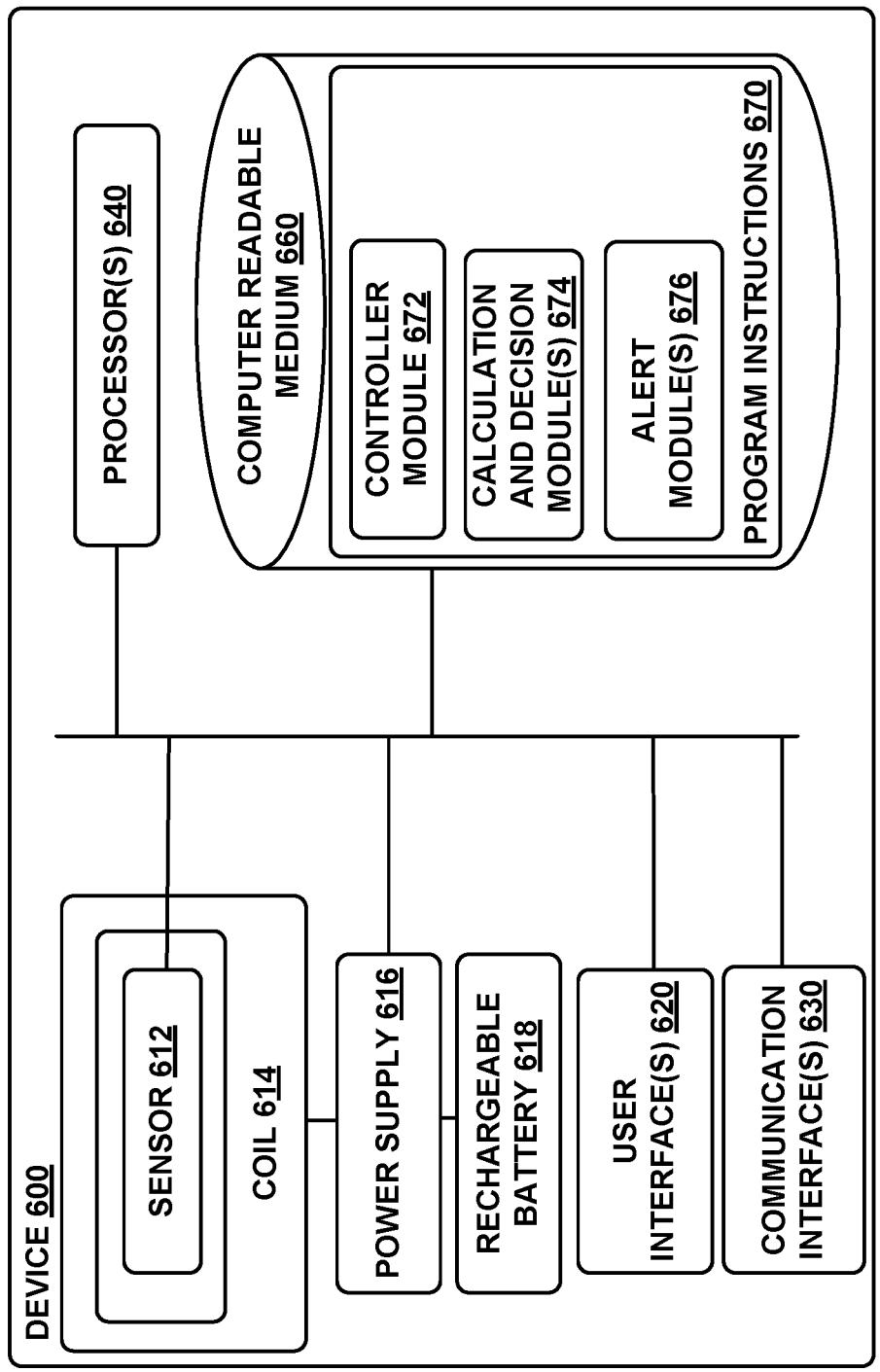
FIG. 6 is a functional block diagram of an example device.

FIG. 6 is a simplified block diagram illustrating the components of a device 600, according to an example embodiment. Device 600 may take the form of or be similar to one of the wearable devices 100, 200, 300, 400, shown in FIGS. 1A-C, 2A-D, 3, and 4A-B. However, device 600 may also take other forms, such as an ankle, waist, or chest-mounted device. Device 600 could also take the form of a device that is not configured to be mounted to a body. For example, device 600 could take the form of a handheld device configured to be maintained in proximity to an environment of interest (e.g., a body part, a biological sample container, a volume of a water treatment system) by a user or operator of the device 600 or by a frame or other supporting structure. Device 600 also could take other forms.

In particular, FIG. 6 shows an example of a device 600 having a sensor 612, a coil 614, a power supply 616, a rechargeable battery 618, a user interface 620, communication interface 630 for transmitting data to a remote system, and processor(s) 640. The components of the device 600 may be disposed on a mount or on some other structure for mounting the device to enable stable detection of one or more properties of an environment of interest (e.g., of a body of a wearer of the device 600), for example, to an external body surface where a portion of subsurface vasculature or other anatomical element is readily observable.

Processor 640 may be a general-purpose processor or a special purpose processor (e.g., digital signal processors, application specific integrated circuits, etc.). The one or more processors 640 can be configured to execute computer-readable program instructions 670 that are stored in the computer readable medium 660 and that are executable to provide the functionality of a device 600 described herein.

The computer readable medium 660 may include or take the form of one or more non-transitory, computer-readable storage media that can be read or accessed by at least one processor 640. The one or more computer-readable storage media can include volatile and/or non-volatile storage components, such as optical, magnetic, organic or other memory or disc storage, which can be integrated in whole or in part with at least one of the one or more processors 640. In some embodiments, the computer readable medium 660 can be implemented using a single physical device (e.g., one optical, magnetic, organic or other memory or disc storage unit), while in other embodiments, the computer readable medium 660 can be implemented using two or more physical devices.

Sensor 612 could include a component configured to detect one or more properties of an environment proximate to the sensor 612 (e.g., skin of an external body surface of a wearer of the device 600) and/or of energy or matter received from the proximate environment. As described above, the sensor 612 may include any component or components capable of detecting at least one property, which could include any properties that may relate to the environment being analyzed by the device (e.g., the body of the wearer or a subsection thereof). For example, the sensor 612 could be configured to measure blood pressure, pulse rate, skin temperature, etc. In some examples, the sensor 612 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. In examples wherein the sensor 612 includes a light sensor, the light sensor could be a photodiode, a photomultiplier, a CCD, a photocell, a photoresistive element, a camera, or any other sensor or sensors configured to detect one or more properties of light emitted by color centers of the functionalized nanodiamonds.

The sensor 612 could additionally include a light source or other energy emitter for transmitting illumination or other energy that can illuminate and/or penetrate the environment to illuminate, excite, or otherwise affect one or more elements of interest in the environment proximate to the sensor 612 (e.g., a fluorescent contrast agent configured to bind to an analyte of interest in blood of a wearer of the device 600). The wavelength of transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission of light by fluorophores, chromophores, or other elements of interest. An energy emitter of the sensor 612 could be configured to produce other forms of energy toward the environment proximate to the sensor 612 that could result in emission, reflection, scattering or some other generation of light or other energy or matter by other chemicals, imaging agents, biological elements, or other analytes proximate to the sensor 612.

Coil 614 comprises windings that are configured to receive electromagnetic energy. The coil 614 is shaped such that the windings of the coil 614 enclose a region of the device 600 wherein the sensor 612 is disposed. The coil 614 can be configured in a number of ways to enable efficient reception of electromagnetic energy using the coil 614 or to enable and/or facilitate a number of other applications. The windings of the coil 614 could be disposed proximate to a peripheral portion of a contact surface of a housing of the device 600 such that an area enclosed by the coil 614 (e.g., a central portion of the contact surface of the housing) is maximized and/or such that a separation distance between the coil 614 and a charging coil of a wireless charger is minimized. The coil 614 could have a rectangular shape, an elliptical shape, or some other shape according to an application; for example, the shape of the coil 614 could correspond to the shape of the contact surface of the housing of the device 600. The coil 614, and/or other components could be configured to enable efficient reception of electromagnetic energy of a specific frequency (e.g., 100 kilohertz to 200 kilohertz) by the coil 614. For example, the coil and a capacitor coupled to the coil 614 could be configured to have a resonant frequency equal to the specific frequency of the electromagnetic energy.

Rechargeable battery 618 is configured to power the device 600 using stored electrochemical energy and to be recharged a plurality of times. The rechargeable battery 618 could include one or more of a variety of rechargeable battery chemistries, including lead-acid, nickel-metal-hydride, nickel-cadmium, lithium-ion, lithium-polymer, or some other rechargeable battery chemistry. Power supply 616 is configured to recharge the rechargeable battery 618 by applying a constant current, a constant voltage, a trickle current, or some other electrical energy having one or more specified properties to two or more electrodes of the rechargeable battery 618. The rechargeable battery 618 could include one or more thermistors that the processor(s) 640, the power supply 616, or some other component of the device 600 could operate to determine a temperature of the rechargeable battery 618 and to prevent damage of the rechargeable battery 618 by reducing a charging rate, a discharging rate, or some other property of use of the rechargeable battery 618 to prevent damage of the rechargeable battery 618.

The power supply 616 is configured to provide power to the device 600 from the rechargeable battery 618 and to recharge the rechargeable battery 618 using electromagnetic energy received using the coil 614. The power supply 616 could include components configured to facilitate the reception of electromagnetic energy by the coil 614. For example, the power supply 616 could include a fixed and/or variable capacitor configured to act as part of an LC tank circuit with the coil 614 such that the LC tank circuit had a resonant frequency substantially equal to a frequency of electromagnetic energy directed toward the coil. In some examples, the power supply 616 could be configured to load the coil 614 or otherwise alter one or more properties of the coil and/or power supply 616 in order to use the coil 614 to communicate with an external system. For example, the power supply 616 could alter a load presented to the coil 614 such that the coil 614 could reflect backscatter electromagnetic radiation toward a wireless charger in order to communicate a charge state, a required power level, or some other property of the coil 614 and/or device 600.

The program instructions 670 stored on the computer readable medium 660 may include instructions to perform any of the methods described herein. For instance, in the illustrated embodiment, program instructions 670 include a controller module 672, calculation and decision module 674 and an alert module 676.

The controller module 672 can include instructions for operating the sensor 612. For example, the controller 672 may operate a light source and/or light sensors of the sensor 612 during each of a set of pre-set measurement periods. The controller module 672 can include instructions for operating the power supply 616 to recharge the rechargeable battery 618 using electromagnetic energy received using the coil 614, to operate the coil 614 to transmit information to another system (e.g., a wireless charger), to route power between the coil 614, the rechargeable battery 618, and other components of the device 600, or to perform other functions. For example, the controller module 672 can include instructions for operating the power supply 616 to apply a pattern of loads to the coil 614 in order to reflect backscatter electromagnetic radiation reflect backscatter electromagnetic radiation toward a wireless charger in order to communicate a charge state, a required power level, or some other property of the coil 614 and/or device 600 (e.g., to communicate information and/or operate the rechargeable battery 618 according to a wireless power transfer standard, e.g., the Qi wireless power transfer standard).

The controller module 672 can also include instructions for operating a user interface 620. For example, controller module 672 may include instructions for displaying data collected by the data collection system 610 and analyzed by the calculation and decision module 674, or for displaying one or more alerts generated by the alert module 676. Further, controller module 672 may include instructions to execute certain functions based on inputs accepted by the user interface 620, such as inputs accepted by one or more buttons disposed on the user interface.

Communication platform 630 may also be operated by instructions within the controller module 672, such as instructions for sending and/or receiving information via a wireless antenna, which may be disposed on or in the device 600. The communication interface 630 can optionally include one or more oscillators, mixers, frequency injectors, etc. to modulate and/or demodulate information on a carrier frequency to be transmitted and/or received by the antenna. In some examples, the device 600 is configured to indicate an output from the processor by modulating an impedance of the antenna in a manner that is perceivable by a remote server or other remote computing device.

Calculation and decision module 672 may include instructions for receiving data from the sensor 612, analyzing the data to determine one or more properties of an environment proximate to the sensor 612 (e.g., of a body of a wearer of the device 600), such as concentration of a target analyte, analyzing the data to determine if a medical condition or other specified condition is indicated, or other analytical processes relating to the environment proximate to the device 600. In particular, the calculation and decision module 672 may include instructions for determining, for each preset measurement time, the presence, concentration, and/or other properties of a clinically-relevant analyte based on the one or more properties of light emitted by contrast agents in a lumen of subsurface vasculature of a user of the device 600; and determining whether a medical condition is indicated based on at least the corresponding presence, concentration, or other property of the clinically-relevant analyte. These instructions could be executed at each of a set of preset measurement times.

The program instructions of the calculation and decision module 672 may, in some examples, be stored in a computer-readable medium and executed by a processor located external to the device 600. For example, the device 600 could be configured to collect certain data regarding physiological parameters from the user and then transmit the data to a remote server, which may include a mobile device, a personal computer, the cloud, or any other remote system, for further processing.

The computer readable medium 660 may further contain other data or information, such as medical and health history of a user of the device 600, that may be useful in determining whether a medical condition or some other specified condition is indicated. Further, the computer readable medium 660 may contain data corresponding to certain physiological parameter baselines, above or below which a medical condition is indicated. The baselines may be pre-stored on the computer readable medium 660, may be transmitted from a remote source, such as a remote server, or may be generated by the calculation and decision module 674 itself. The calculation and decision module 674 may include instructions for generating individual baselines for the user of the device 600 based on data collected over a certain number of measurement periods. For example, the calculation and decision module 674 may generate a baseline concentration of a pulse rate and galvanic skin resistance for each of a plurality of measurement periods by averaging the pulse rate and galvanic skin resistance at each of the measurement periods measured over the course of a few days, and store those baseline pulse rates and galvanic skin resistances in the computer readable medium 660 for later comparison. Baselines may also be generated by a remote server and transmitted to the device 600 via communication interface 630. The calculation and decision module 674 may also, upon determining that a medical or other emergency condition is indicated, generate one or more recommendations for the user of the device 600 based, at least in part, on consultation of a clinical protocol. Such recommendations may alternatively be generated by the remote server and transmitted to the device 600.

In some examples, the collected physiological parameter data, baseline profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 674 that a medical or other specified condition is indicated, the alert module 676 may generate an alert via the user interface 620. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
    a housing, wherein the housing includes a contact surface for contacting an external body surface;
    a rechargeable battery disposed within the housing;
    a physiological sensor;
    a coil that receives electromagnetic energy, wherein the coil is disposed within the housing proximate to the contact surface of the housing, wherein the coil comprises a plurality of windings that surround the physiological sensor;
    a magnetic shield, wherein the magnetic shield is disposed within the housing between the coil and the rechargeable battery; and
    electronics disposed in the wearable device, wherein the electronics comprises:
        a recharger, wherein the recharger is powered by electromagnetic energy received by the coil to recharge the rechargeable battery; and
        a controller that operates the physiological sensor to detect one or more physiological parameters via the external body surface.

2. The wearable device of claim 1, wherein the magnetic shield is wider than the coil so as to extend beyond the windings of the coil by at least 0.5 millimeters.

3. The wearable device of claim 1, wherein the magnetic shield is disposed between the physiological sensor and the rechargeable battery, and wherein at least one component of the electronics is disposed opposite the magnetic shield from the coil and the physiological sensor.

4. The wearable device of claim 1, further comprising a flexible interconnect that electrically couples the at least one component of the electronics to at least one of the coil or the physiological sensor.

5. The wearable device of claim 4, wherein the magnetic shield has a hole therein, and wherein the flexible interconnect passes through the hole in the magnetic shield.

6. The wearable device of claim 1, wherein the physiological sensor comprises a light sensor.

7. The wearable device of claim 6, wherein the physiological sensor further comprises at least one light emitter.

8. The wearable device of claim 7, wherein the physiological sensor is a blood oxygenation and pulse oximetry sensor.

9. The wearable device of claim 1, wherein the physiological sensor comprises electrical contacts for detecting a galvanic skin resistance of skin at the external body surface.

10. The wearable device of claim 1, wherein the external body surface is a wrist location.

11. The wearable device of claim 1, further comprising a printed circuit board disposed within the housing, wherein the coil comprises at least one trace on the printed circuit board.

12. The wearable device of claim 1, wherein the printed circuit board is a flexible printed circuit board.

13. The wearable device of claim 1, further comprising a user interface configured to provide a user-discernible indication of the one or more physiological parameters.

14. The wearable device of claim 1, further comprising a wireless communication interface configured to transmit data indicative of the one or more physiological parameters.

15. The wearable device of claim 1, wherein the housing is water-proof.

16. The wearable device of claim 1, further comprising:
a mount for mounting the housing to the external body surface such that the contact surface of the housing is in contact with the external body surface.

17. The wearable device of claim 1, wherein the contact surface of the housing includes a window proximate the physiological sensor.

18. The wearable device of claim 1, further comprising a printed circuit board disposed within the housing, wherein the physiological sensor and the coil are mounted on the printed circuit board.

* * * * *